United States Patent [19]

Sharif

[11] Patent Number: 5,182,408
[45] Date of Patent: Jan. 26, 1993

[54] PROCESS FOR PREPARATION OF STABLE AQUEOUS SOLUTIONS OF ZIRCONIUM CHELATES

[75] Inventor: Sharif Sharif, Midland, Tex.

[73] Assignee: Zirconium Technology Corporation, Midland, Tex.

[21] Appl. No.: 691,363

[22] Filed: Apr. 25, 1991

[51] Int. Cl.$^5$ ................................................ C07F 7/00
[52] U.S. Cl. ...................................................... 556/55
[58] Field of Search ........................................... 556/55

[56] References Cited

U.S. PATENT DOCUMENTS

| | | | |
|---|---|---|---|
| 4,460,751 | 7/1984 | Hanlon et al. | 525/371 |
| 4,477,360 | 10/1984 | Almond | 252/8.551 |
| 4,692,254 | 9/1987 | Kucera | 252/8.551 |
| 4,958,038 | 9/1990 | Smeltz | 556/55 |

FOREIGN PATENT DOCUMENTS 0004784 4/1965 Japan ..................... 556/55

Primary Examiner—José G. Dees
Assistant Examiner—Porfirio Nazario
Attorney, Agent, or Firm—Robert C. Peterson

[57] ABSTRACT

The present invention comprises reacting ammonium, sodium or potassium hydroxide or water soluble amines or amine derivatives with alpha-hydroxy carboxylic acid to prepare a neutral solution of the corresponding alpha-hydroxy carboxylic salt in a stoichiometric reaction.

The alkali metal, ammonium, amine or amine derivative, alpha-hydroxy carboxylic acid salt is then added to solutions of zirconium which may be zirconium oxychloride, zirconium hydroxy chloride, zirconium acetate and the like, ammonia, water soluble amines or amine derivatives, diisopropylamine or a mixture of two or more of these bases, as well as soluble carbonates and/or bicarbonates of ammonium and alkali metals such as sodium and potassium, while mixing the solutions. The procedure produces a mildly acidic or basic solution of the zirconium alpha-hydroxy carboxylic chelate.

10 Claims, No Drawings

PROCESS FOR PREPARATION OF STABLE AQUEOUS SOLUTIONS OF ZIRCONIUM CHELATES

SUMMARY OF THE INVENTION

The invention relates to a novel process for the preparation of stable aqueous solutions of zirconium chelates at 100% chemical yield without effluent or solid waste. The novel zirconium chelate solutions are stable towards the addition of acids, bases, boiling, dilution and aging.

BACKGROUND OF THE INVENTION

These chelates may be used in the paper coating industry or as starch and protein insolubilizers, and in the petroleum industry for fracing petroleum bearing formations.

The chelates are used in both aqueous and non-aqueous solutions to retain metals in solution at high temperatures and over wide pH ranges and remaining compatible with other chemicals. Chelates can be of transition metals such as titanium, zirconium, copper, iron, and the like. Also aluminum and boron chelates react similar to transition metal chelates.

Particularly in the petroleum industry, chelates are used in cross-linking gels such as discussed by Almond in U.S. Pat. No. 4,477,360, Method and Compositions for Fracturing Subterranean Formations. The patentee discloses an aqueous gel containing a retarded cross-linking composition comprising a zirconium salt or chelate and a polyhydroxyl containing compounds. Typically referred to as polyols. Almond describes the useful polyol examples as glycerol, erythritol, threitol, ribitol, and others. Almond suggests that the polyhydroxyl containing compound useful in his process is admixed with an aqueous fluid and a cross-linking compound featuring zirconium chelates. He also points out that the constituents of the retarded cross-linking composition can be admixed in any order, in any conventional mixing apparatus. The gelling agents employed by Almond include gum guar, locust bean gum, karaya gum, sodium carboxymethylguar and several other compounds of guar.

Smeltz, U.S. Pat. No. 4,958,038 issued Sep. 18, 1990, describes a process which comprises combining glycerol, erythritol, arabitol, etc. and lactic acid, glycolic acid, malic acid, citric acid, tartaric acid, saccharic acid, gluconic acid, glyceric acid or mandelic acid to provide an aqueous solution of polyol and alpha-hydroxy carboxylic acid, and then at an alkaline pH of 10 or less reacting the solution with a titanium compound of an inorganic acid at an alpha-hydroxy carboxylic acid to titanium mol ratio between 0.5 to 1 and about 4 to 1 and a polyol to titanium mol ratio between about 0.25 to 1 and about 2 to 1. In fracing oil wells, Smeltz uses solvatable polysaccharides which include guar gum and locust bean gum, as well as other galactomannan and glucomannan gums, such as those derived from sennas, Brazilwood, Tera, Honey locust, Karaya gum and the like.

Hanlon et al, U.S. Pat. No. 4,460,751 describes a crosslinker which is made by preparing an alpha-hydroxy carboxylic acid solution, then adding a zirconium compound, e.g. zirconium oxychloride to form a second mixture, and finally adds the amine compound to the mixture. If zirconium carbonate is used, the zirconium carbonate is added to water to form a first mixture, next the amine compounded is added to form a second mixture, and finally the alpha-hydroxy carboxylic acid is added to the second mixture. Of course, Hanlon is not using chelates in his crosslinking composition.

Examples of the previous nonadvantageous methods of preparing zirconium chelates involves the use of dangerous solvents, such as ethers and alcohols, for producing zirconium triethanolamine chelates via zirconium n-propyl zirconate soluablized in n-propanol. This method involves the soluablization of zirconium tetrachloride which is also a dangerous chemical in n-propanol or ether followed by reacting it with triethanolamine. See Kucera, U.S. Pat. No. 4,692,254 describing such methods in detail.

Also aqueous chelates are produced through the separation of insoluble chelates as intermediates such as zirconium citrate, zirconium lactate and zirconium tartrate. This process generates effluents such as sodium sulphate, ammonium sulphate or other anions such as chlorides, nitrates, etc. See Van Mater, U.S. Pat. No. 2,498,514 describing such methods in more detail.

The prior methods of preparing zirconium chelates for preparation of solutions useful in fracing oil and gas strata have encountered such problems as low chemical yield, a need for an organic solvent which causes fire hazard and may produce toxic fumes or exhibits poor stability on aging and/or dilution, exposure to the atmospheric conditions, dilution with water, boiling and/or the addition of inorganic acids or bases. Also, such prior preparation methods have generated organic and/or inorganic effluent and/or solid waste.

The present invention relates to a new process for preparing zirconium chelate solutions which are stable on the addition of acids, bases, on boiling, at high dilution and/or aging; and therefor are useful in a wide range of industrial applications, especially in the areas of the paper coating industry and frac solutions for treating underground oil or gas bearing strata.

DETAILED DESCRIPTION OF THE INVENTION

The process of the present invention utilizes solutions of zirconium such as zirconium oxychloride, zirconium hydroxy chloride, zirconium acetate and the like, ammonium, water soluble amines or amine derivatives such as triethanolamine and diisopropylamine or a mixture of two or more of these bases. Also an alkali metal hydroxide such as sodium or potassium hydroxide, and an alpha-hydroxy carboxylic acid such as lactic, tartaric or citric acid are utilized.

The present invention involves the stoichiometric reaction between ammonium, sodium or potassium hydroxides or water soluble amines or amine derivatives with alpha-hydroxy carboxylic acid, such as lactic, citric or tartaric acid to prepare a neutral solution of the corresponding alpha-hydroxy carboxylic salt. The obtained alkali metal, ammonium, or amine (or amine derivative) alpha-hydroxy carboxylic salt is then added to a solution of zirconium which may be zirconium oxychloride, zirconium hydroxy chloride, zirconium acetate or the like. This procedure produces a mildly acidic or basic solution of the corresponding zirconium alpha-hydroxy carboxylic chelate. Alternatively, the alpha-hydroxy carboxylic salt may be pre-prepared and added in solid or liquid form to the zirconium starting material. In each situation, the last step of the process is the addition of the alpha-hydroxy carboxylic salt to the zirconium compound selected from the group consisting of zirconium hydroxychloride, zirconium oxychloride, zirconium oxynitrate, zirconium hydroxynitrate, ammonium zirconium carbonate, zirconium acetate, zirconium oxybromide, zirconium hydroxybromide and mixtures thereof.

It should be noted that the claimed processes have 100% chemical yield and do not generate either organic and/or inorganic effluent and/or solid waste. The process utilizes only aqueous chemicals to produce purely aqueous products which eliminate the need for organic solvents and the attendant fire hazards and other disadvantages.

EXAMPLE 1

(i) In 2000 ml glass beaker 818.9 gm of 88% lactic acid was weighed out. The beaker was placed on a magnetic srirrer and the lactic acid was agitated using a magnetic bar.

(ii) Gradually 485.7 gm of ammonium hydroxide solution was added to prepare of ammonium lactate. In this mixture the $NH_3$ to lactate molar ratio is 1.0 to 1.0, based on 88% acid and 28.0% $NH_3$ in the lactic acid and the ammonium hydroxide solution, respectively. This neutralization reaction is exothermic and the addition of the ammonium hydroxide solution must be slow enough to avoid any boil-over. The temperature of the produced ammonium lactate solution was between 150–200 degrees F.

(iii) In a 4000 ml glass beaker 1000 gm of zirconium chloride hydroxide solution was weighed and mixing was started. Gradually, the above hot ammonium lactate solution was added to the zirconium chloride hydroxide solution while mixing. After all of the ammonium lactate solution was added, the solution was mixed for and additional 15 minutes. When the reaction batch was cooled to room temperature, its pH was between 5.0–7.0 at this stage of the preparation. The temperature of ammonium lactate solution before its addition to zirconium chloride hydroxide has been found to have no effect on the quality of the product.

(iv) The produced intermediate was almost a neutral solution of ammonium zirconium lactate which assays 8.7% $ZrO_2$ at a lactate to Zirconium molar ratio of 5.0 to 1.0.

The obtained product was stable on boiling, aging, dilution and when its pH was altered (by the addition of HCl or ammonium hydroxide) in the range of 3.0–10.0. The lactate to Zirconium molar ratio was 5.0 to 1.0.

EXAMPLE 2

(i) In a suitable beaker 315.2 gm of sodium citrate dihydrate was dissolved in 598.4 gm of distilled water and a clear solution was obtained. This solution of sodium citrate can also be obtained by mixing sodium hydroxide solution with citric acid solution or citric acid solids with sodium hydroxide solution or by mixing sodium hydroxide solids with citric acid solution.

(ii) The above sodium citrate solution was added to 500 gm of zirconium hydroxychloride solution which contains 20.0% $ZrO_2$. The reaction batch was mixed continuously while the sodium citrate was being added. A clear solution of sodium zirconium citrate was obtained after the addition of sodium citrate solution was completed. The pH of the solution product was 6.2.

(iii) 23 gm of 50% sodium hydroxide was added to raise the product pH to 9.0. The citrate to Zirconium molar ratio in this product was 1.34 to 1.00. The product contained 7.0% $ZrO_2$ and was stable on boiling, aging and dilution to very low $ZrO_2$ concentrations.

The starting zirconium material in example (1) and (2) was zirconium hydroxychloride, however, any one or mixtures of the following zirconium chemicals may be used:

(i) Zirconium Oxychloride
(ii) Zirconium Oxynitrate
(iii) Zirconium Hydroxynitrate
(iv) Ammonium Zirconium Carbonate
(v) Zirconium Acetate
(vi) Zirconium Oxybromide
(vii) Zirconium Hydroxybromide Also a mixture of zirconium hydroxychloride and any or all of the above zirconium starting materials can be used in the preparation of similar products.

EXAMPLE 3

(i) In a suitable beaker 630 gm of sodium citrate dihydrate was dissolved in 1196 gm of distilled water.

(ii) The above sodium citrate solution was added to 1000 gm of zirconium oxychloride solution which contained 20% $ZrO_2$. A clear solution with a pH of 5.3 was obtained.

(iii) 104 gm of 50% sodium hydroxide was added while mixing to raise the product pH to 9.0. $ZrO_2$ content in the product was 6.8%. Good stability of the obtained solution was observed on boiling, aging, dilution and the addition of acids and bases to alter the pH between 3.0 and 10.0. The citrate to Zirconium molar ratio in this product was 1.34 to 1.00.

The alpha-hydroxy carboxylic acid to Zirconium molar ratio can vary between 0.5–20.0 to 1.0 and the $ZrO_2$ concentration in the products using these methods can vary between 0.5–17%.

EXAMPLE 4

(i) 97.1 gm of 28% ammonium hydroxide solution was mixed with 163.8 gm of 88% lactic acid to prepare ammonium lactate solution.

(ii) The above ammonium lactate solution was added to 500 gm of zirconium hydroxychloride solution which contains 20% $ZrO_2$ while mixing. A clear solution with a pH of 4.3 was obtained.

(iii) 154 gm of 28% ammonium hydroxide solution was added to establish a pH of 9.0 in the final solution product. The $ZrO_2$ content in the product was 10.9%. This ammonium zirconium lactate solution was stable on boiling, aging, dilution and the addition of bases and acids to alter the pH between 3.0–10. The lactate to Zirconium molar ratio was 2.0 to 1.0.

EXAMPLE 5

(i) In a suitable beaker 120 gm of granular tartaric acid was dissolved in 300 gm of distilled water.

(ii) 359 gm of 25% potassium hydroxide solution was mixed with the above tartaric acid solution to prepare potassium tartrate solution.

(iii) The above potassium tartrate solution was added to 500 gm of zirconium hydroxychloride solution which contains 20% $ZrO_2$ while mixing.

(iv) After the addition of the potassium tartrate solution was completed a clear solution of potassium zirconium tartrate was obtained. The pH of the product was 4.0 and it contains 7.8% $ZrO_2$. The tartrate to Zirconium molar ratio in the product was 1.0 to 1.0.

EXAMPLE 6

(i) In a suitable beaker 1809 gm of triethanolamine was mixed with 219 gm of 88% lactic acid.

(ii) The blend from (i) of this example was then added to 445 gm of zirconium oxynitrate which contains 20% $ZrO_2$ while mixing.

(iii) After the addition of lactic acid-triethanolamine blend was completed, a clear and stable solution of triethanolamine zirconium lactate was obtained.

(iv) pH of the product was 8.2, had 3 to 1 lactate to Zirconium molar ratio and contained 3.6% $ZrO_2$.

EXAMPLE 7

(i) 189 gm of 88% lactic acid was mixed with 122 gm of 50% sodium hydroxide solution to prepare sodium lactate solution.

(ii) The above sodium lactate solution was added to 510 gm of zirconium hydroxychloride solution which contains 15.2% $Zr_2$ while mixing.

(iii) After the addition of the sodium lactate was completed a clear solution of sodium zirconium lactate was obtained. pH of the product was 5.8, contained 9.5% $ZrO_2$ and had a lactate to Zirconium molar ratio of 3.0 to 1.0.

EXAMPLE 8 pH of the product from Example 7 was increased to 10.0 by the addition of 50% NaOH to yield stable high pH solution of sodium zirconium lactate at a lactate to Zirconium molar of 3.0 to 1.0.

EXAMPLE 9 pH of the product from Example 7 was lowered to 3.0 by the addition of hydrochloric acid to yield a stable, low pH product at a lactate to Zirconium molar ratio of 3.0 to 1.0.

EXAMPLE 10

755.9 gm of 28% ammonium hydroxide solution was added to 409.5 gm of 88% lactic acid to prepare sodium lactate solution.

The produced sodium lactate solution was added to 500 gm of zirconium oxynitrate solution which contained 20.0% $ZrO_2$, while mixing. A clear solution product of sodium zirconium lactate was obtained. The product had a pH of 7.5 and it contained 6.0% ZrO. The lactate to zirconium molar ratio in the solution product was 5.0 to 1.0.

The product was stable on the addition of acids or bases, dilution, boiling and/or aging.

EXAMPLE 11

506.9 gm of 28% ammonium hydroxide solution was added to 409.5 gm of 88% lactic acid to prepare ammonium lactate solution.

The above ammonium lactate solution was added to 500 gm of zirconium hydroxynitrate solution which contained 20.0% $ZrO_2$. A clear and stable solution of ammonium zirconium lactate was obtained. The solution product had a pH of 5.3 and it contained 7.0% $ZrO_2$. The lactate to zirconium molar ratio in the product was 5.0 to 1.0.

The product was stable on the addition of acids or bases, dilution, boiling, and/or aging.

EXAMPLE 12

396.9 gm of 50% sodium hydroxide solution was added to 410 gm of 88% lactic acid to prepare sodium lactate solution.

The above sodium lactate solution was added to 500 gm of zirconium hydroxynitrate which contains 20.0% $ZrO_2$. A stable solution of sodium zirconium lactate with a pH of 10.4 was obtained. The product had a lactate to zirconium molar ratio of 5.0 to 1.0 and it was stable on the addition of acids or bases, dilution, boiling, and/or aging. The solution product was assayed 7.0% $ZrO_2$.

EXAMPLE 13

80.7 gm of 50% sodium hydroxide solution was added to 103.3 gm of 88% lactic acid to prepare sodium lactate solution.

The above solution was added to 230 gm of zirconium acetate solution which contained 22.0% $ZrO_2$, while mixing. A stable solution of sodium zirconium lactate with a pH of 6.2 was obtained. The solution product assayed 12.2% $ZrO_2$ and it was stable on the addition of acids or bases, dilution, boiling, and/or aging. The lactate to zirconium molar ratio in the product was 2.5 to 1.0.

The methods set forth in the foregoing examples are used to make the following list of chelates:

Sodium Zirconium Tartrate
Sodium Zirconium Glycolate
Sodium Zirconium Maliate
Sodium Zirconium Saccharate
Sodium Zirconium Gluconate
Sodium Zirconium Glycerate
Sodium Zirconium Mandelate
Ammonium Zirconium Citrate
Potassium Zirconium Glycolate
Potassium Zirconium Maliate
Potassium Zirconium Saccharate
Potassium Zirconium Gluconate
Potassium Zirconium Glycerate
Potassium Zirconium Mandelate
Amine (or amine derivative) Zirconium Citrate
Amine (or amine derivative) Zirconium Tartrate
Amine (or amine derivative) Zirconium Glycolate
Amine (or amine derivative) Zirconium Maliate
Amine (or amine derivative) Zirconium Saccharate
Amine (or amine derivative) Zirconium Gluconate
Amine (or amine derivative) Zirconium Glycerate
Amine (or amine derivative) Zirconium Mandelate The compositions obtained by the methods disclosed herein are highly stable on boiling, aging, dilution to low $ZrO_2$ concentrations and maintain stability over a pH range of 3 to 10.

Although certain preferred embodiments of the invention have been described herein for illustration, it will be appreciated that various modifications and changes of the procedures and compositions recited may be implemented without departing from the principles. Such changes are therefore deemed to lie within the scope and spirit of the invention except as may be necessarily limited by the appended claims.

What is claimed is:

1. A method of preparing zirconium chelates which comprises
   a. reacting ammonium hydroxide, sodium hyroxide, potassium hydroxide, water soluble amines or amine derivatives or alkali metal carbonates or bicarbonates with an alpha hydroxy carboxylic acid to prepare an almost neutral solution of the corresponding alpha hydroxy carboxylic salt;
   b. adding said alpha hydroxy carboxylic salt to a solution of zirconium oxychloride, zirconium hydroxy chloride, zirconium acetate or mixtures thereof to form a zirconium chelate.

2. The method of claim 1 wherein stoichiometric quantities of the reactants are used to produce zirconium chelates.

3. The method of claim 1 wherein the zirconium chelate has a pH in the range of 3 to 10.

4. The method of claim 1 wherein the alpha-hydroxy carboxylic acid to zirconium molar ratio is between 0.5–20 to 1.0.

5. The method of claim 1 wherein the zirconium dioxide concentration is from 0.5 to 17 percent.

6. A method of preparing zirconium chelates which comprises
   a. dissolving an alpha hydroxy carboxylic salt of sodium, potassium, ammonia or water soluble amine or amine derivative, alkali metal carbonates or bicarbonates in water to form a clear solution; and
   b. adding said alpha hydroxy carboxylic salt while mixing to a solution of zirconium hydroxychloride, zirconium oxychloride, zirconium oxynitrate, zirconium hydroxynitrate, ammonium zirconium carbonate, zirconium acetate, zirconium oxybromide, zirconium hydroxybromide or mixtures thereof to form a zirconium chelate.

7. The method of claim 6 wherein stoichiometric quantities of the reactants are used to produce zirconium chelates.

8. The method of claim 6 wherein the zirconium chelate has a pH in the range of 3 to 10.

9. The method of claim 6 wherein the alpha-hydroxy carboxylic acid to zirconium molar ratio is between 0.5–20 to 1.0.

10. The method of claim 6 wherein the zirconium dioxide concentration is from 0.5 to 17 percent.

* * * * *